United States Patent [19]

Jacobine et al.

[11] Patent Number: 5,182,360
[45] Date of Patent: Jan. 26, 1993

[54] TRIS(NORBORNENYL) ISOCYANURATE

[75] Inventors: Anthony F. Jacobine, Meriden; Steven T. Nakos, Andover, both of Conn.

[73] Assignee: Loctite Corporation, Hartford, Conn.

[21] Appl. No.: 778,007

[22] Filed: Oct. 17, 1991

[51] Int. Cl.$^5$ .................... C08G 75/04; C07D 251/34
[52] U.S. Cl. ...................... 528/205; 544/193; 544/215; 522/167; 526/261; 528/263; 528/376
[58] Field of Search ............... 544/221, 215; 522/167; 526/261; 528/205, 363, 376

[56] References Cited

U.S. PATENT DOCUMENTS

| | | | |
|---|---|---|---|
| 3,396,167 | 8/1968 | Davies | 544/221 |
| 3,450,701 | 6/1969 | Davies | 544/221 |
| 3,661,744 | 5/1972 | Kehr et al. | 522/97 |
| 3,892,643 | 7/1975 | Tanaka et al. | 522/167 |
| 4,119,617 | 10/1978 | Hanyuda et al. | 528/360 |
| 4,808,638 | 2/1989 | Steinkraus et al. | 522/24 |
| 5,034,490 | 6/1991 | Jacobine et al. | 528/30 |

OTHER PUBLICATIONS

Jacobine et al., *Proceedings of ACS Division of Polymeric Materials: Science and Engineering*, vol. 60, pp. 211–216 (1989).

Jacobine et al., "Photoinitiated Cross-linking of Norbornene Resins with Multifunctional Thiols", Chapter 13 of *Radiation Curing of Polymeric Materials*, ACS Symposium Series #417, American Chemical Society, 1990.

Diveley et al., *J. Org. Chem.*, 34, 616–623 (1969).
Ulrich, et al., *Newer Methods of Preparative Organic Chemistry*, XI, 280–315 (1971).

*Primary Examiner*—Marion E. McCamish
*Assistant Examiner*—Arthur H. Koeckert
*Attorney, Agent, or Firm*—Vidas & Arrett

[57] ABSTRACT

Tris(norbornenyl) isocyanurate compounds of the formula:

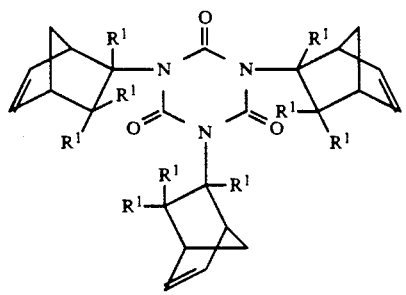

wherein $R^1$ is either H or methyl group, are prepared from the base-catalyzed trimerization of norbornenyl isocyanate. Tris(norbornenyl) isocyanurate is suitable for use as a crosslinker in thiol-ene formulations containing a difunctional thiol oligomer or in systems containing norbornene-difunctional oligomers and polyfunctional thiols, producing improved high temperature properties for the cured compositions.

7 Claims, 2 Drawing Sheets

TRIS(NORBORNENYL) ISOCYANURATE

FIELD OF THE INVENTION

The invention pertains to a novel tris(norbornenyl) isocyanurate ("TNI") compound and its application to thiol-ene formulations containing a difunctional thiol oligomer or systems containing norbornene-difunctional oligomers and polyfunctional thiols.

BACKGROUND OF THE INVENTION

Norbornenyl functional resins and their uses are described in U.S. Pat. No. 4,808,638 and references cited therein. The disclosed use of such resins in this reference is as the polyene resin in radically cured thiol-ene formulations. The aforementioned U.S. patent is incorporated herein by reference.

Further norbornenyl functional compounds useful in thiol-ene compositions as described in U.S. Pat. No. 4,808,638 are disclosed in U.S. Pat. No. 5,034,490 and copending applications Ser. No. 07/315,737 filed Feb. 24, 1989, Ser. No. 07/619,068 filed Nov. 28, 1990, and Ser. No. 07/648,585 filed Jan. 31, 1991.

Tris(norbornenyl) isocyanurate is a previously unreported compound.

Isocyanurate linkages have been reported to improve high temperature properties of polyurethane foams.

SUMMARY OF THE INVENTION

In one aspect the invention comprises a novel tris(norbornenyl) isocyanurate compound having the formula:

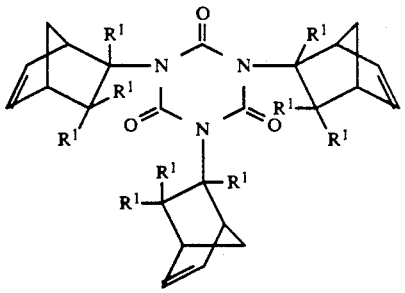

wherein $R^1$ is either H or methyl group, prepared from the base-catalyzed trimerization of norbornenyl isocyanate.

A second aspect of the invention comprises a process for producing the tris(norbornenyl) isocyanurate of the invention involving the trimerization of norbornenyl isocyanate catalyzed by potassium t-butoxide. This process produces no byproducts, either solid or liquid.

Tris(norbornenyl) isocyanurate is suited for use in curable thiol-ene formulations of the type described in U.S. Pat. No. 4,808,638. In U.S. Pat. No. 4,808,638 there are described photocurable thiolene compositions comprising a norbornene functional resin, a polythiol and a free radical photoinitiator. Further description of this system may be found in Jacobine et al, *Proceedings of ACS Division of Polymeric Materials: Science and Engineering*, Vol. 60, pp. 211–216 (1989). TNI is particularly suited for use as a crosslinker in thiol-ene formulations containing a difunctional thiol oligomer or in systems containing norbornene-difunctional oligomers and polyfunctional thiols. Thus, a further aspect of the invention is a curable thiol-ene composition in which TNI is added, thereby incorporating the isocyanurate linkage into the cured matrix, providing improved high temperature properties.

DETAILED DESCRIPTION OF THE INVENTION

Figure 1:
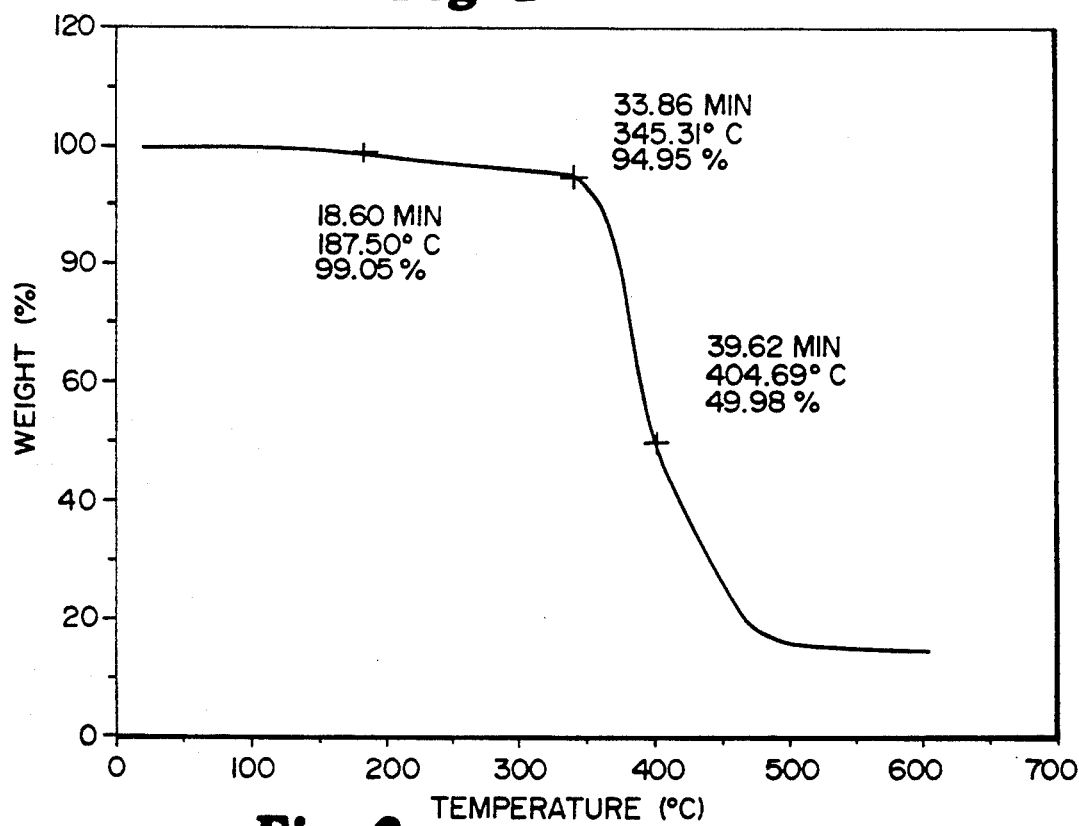
FIG. 1 is a TGA trace of a NM-N control formulation described in Example 2.

The tris(norbornenyl) isocyanurate compound of the invention may be represented by the formula:

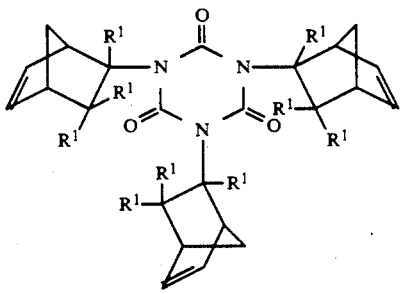

wherein $R^1$ is either H or methyl group. The inventive tris(norbornenyl) isocyanurate compound may be prepared from the base-catalyzed trimerization of norbornenyl isocyanate. Tris(norbornenyl) isocyanurate is suitable for use as a crosslinker in thiol-ene formulations containing a difunctional thiol oligomer or in systems containing norbornene-difunctional oligomers and polyfunctional thiols.

The plural norbornene functional compounds useful in the invention are known from U.S. Pat. No. 4,808,638, incorporated herein by reference, and have recently also been described in Jacobine et al, "Photoinitiated Cross-linking of Norbornene Resins with Multifunctional Thiols", Chapter 13 of *Radiation Curing of Polymeric Materials*, ACS Symposium Series #417, American Chemical Society, 1990, also incorporated herein by reference. Particularly preferred norbornene compounds are norbornenemethyl norbornenecarboxylate, norbornene carboxylate esters of polyols such as 1,6-hexanediol, trimethylolpropane, ethoxylated bisphenol A, and mixtures thereof.

The polythiol component of the inventive compositions may be any compound having two or more thiol groups per molecule. Suitable polythiols are described in U.S. Pat. No. 3,661,744 at col.8, In 76-col.9, In 46; in U.S. Pat. No. 4,119,617, col.7, Ins 40-57; U.S. Pat. No. 3,445,419; and U.S. Pat. No. 4,289,867. Especially preferred are polythiols obtained by esterification of a polyol with an α or β-mercaptocarboxylic acid such as thioglycolic acid, or β-mercaptopropionic acid. Particularly preferred polythiols are pentaerythritol tetramercaptoacetate and pentaerythritol tetrakis-β-mercaptopropionate (PETMP).

The ratio of the polyene to the polythiol component can be varied widely. Generally it is preferred that the ratio of thiol to ene groups be between 0.7:1 and 1.3:1, but ratios outside this range may occasionally be usefully employed without departing from the invention hereof.

The use of tris(norbornenyl) isocyanurate in thiol-ene formulations containing a difunctional thiol oligomer or in systems containing norbornene-difunctional oligomers and polyfunctional thiols provides improved high temperature properties, including increased shear storage modulus in temperature ranges of 46°-82° C., compared to formulations without a TNI additive.

The invention may be illustrated by the following non-limiting examples:

EXAMPLE 1

Preparation of Tris(Norbornenyl) Isocyanurate

The tris(norbornenyl) isocyanurate compound of the present invention is prepared from an adaptation of a procedure for synthesizing trisopropyl isocyanurate by the trimerization of norbornenyl isocyanate:

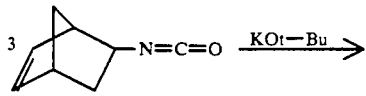

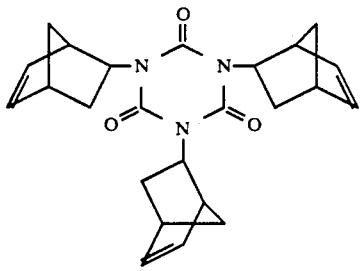

Norbornenyl isocyanate (10.0 g, 0.074 mole) and 0.2 g potassum t-butoxide in 25 ml DMF were heated to 100° C. for three hours. Upon cooling, some of the crude product precipitated, which was removed by filtration. It was recrystallized from dry ethanol/toluene to give 3.7 g of product. Solvent from the mother liquor was removed by rotary evaporation to give an oil, which was redissolved in 5 ml toluene, then filtered to remove insolubles. The filtrate was triturated with dry ethanol to give additional precipitated product which was isolated by filtration. The combined product yield was 4.7 g (47%) of off-white crystals with a melting point of 152°-155° C. No liquid or solid byproducts are produced by the reaction.

The starting material, norbornenyl isocyanate is a known compound. It may be prepared by the standard method of phosgenation of the parent amine. Alternatively, it may be prepared by reacting norbornenecarbonyl chloride with sodium azide and then thermally rearranging the reaction product thereof to the isocyanate.

EXAMPLE 2

Two separate analyses were performed to determine the formulated properties of tris(norbornenyl) isocyanurate (TNI), namely TGA data and temperature sweep DMA data. Due to its intractability, TNI was dissolved in norbornenemethyl norbornenecarboxylate (NM-N) 50/50 (w/w) (II) and compared it with NM-N alone (I).

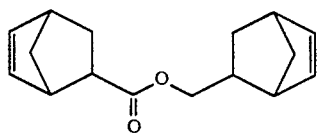

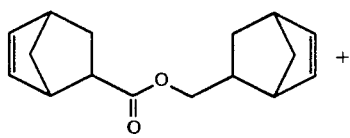

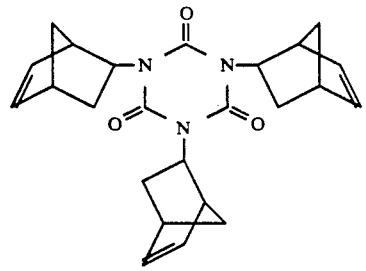

| Preparation of Norbornenemethyl Norbornenecarboxylate (NM-N)(I) Amounts | | | |
|---|---|---|---|
| Compound | Weight | Moles | Wt. % |
| Norbornene Carboxaldehyde | 1,000.0 g | 8.18 | — |
| Aluminum Isopropoxide | 10.0 g | — | 2.0 |

Procedure

5-Norbornene-2-carboxaldehyde was added, rapidly at first, then more slowly to 20.0 g aluminum isopropoxide mechanically stirred with N₂ blanket. A temperature of 50° C. was maintained with gentle external cooling during the addition. After the addition, the reaction was held at 60° C. for two hours and allowed to stir overnight at room temperature. The reaction mixture was diluted with 2000 ml of hexane, and extracted with 3×400 ml water portions. Filtration through Celite was necessary to observe phases. The organic layer was stripped to remove the solvent, then vacuum distilled with an air condenser. After removal of approximately 70 g of a liquid forecut, the solid product was distilled at 113°-118° C. at 0.05 mm Hg. Yield: 776.94 g (78%) of a translucent solid.

| Preparation of Tris(Norbornenyl) Isocyanurate Amounts | | | |
|---|---|---|---|
| Compound | Weight | Moles | Wt % |
| Norbornenyl Isocyanate | 100.0 g | 0.74 | — |
| Potassium t-butoxide | 2.0 g | — | 2.0 |

Procedure

The above listed compounds were mixed with 250 ml DMF and heated to 100° C. for six hours under N₂ blanket. After filtering to remove the product, the dark solid was recrystallized from ethanol and a small amount of toluene and dried for 3 hours in a vacuum dessicator. Yield: 44.07 g (44%) of tan crystals, with a mp of 158°-162° C.

The following formulations were UV cured into 70 mil films:

| Formulation (II): | |
|---|---|
| TNI: | 7.5 g (55.4 meq Norbornene) |
| NM-N: | 7.5 g (61.35 meq Norbornene) |
| PETMP: | 14.25 g (116.84 meq SH) |
| Darocur ® 1173:* | 0.60 g |

Darocur ® 1173 is an acetophenone based photoinitiator sold by EM Chemicals, Hawthorne, N.Y.

The above listed components were dissolved by heating in a glass beaker, and poured onto a preheated (5 hours at 90° C.) mold setup with a 70 mil spacer clamp. A 70 mil (1.75 mm) film was cured by UV irradiation (2530 mJ/cm² per side) from a medium pressure Hg lamp. A transparent, dry-to-the-touch film resulted.

| Formulation (I): | |
|---|---|
| NM-N: | 15.0 g (122.7 meq Norbornene) |
| PETMP: | 14.96 g (122.7 meq SH) |
| Darocur ® 1173: | 0.61 g |

Figure 2:
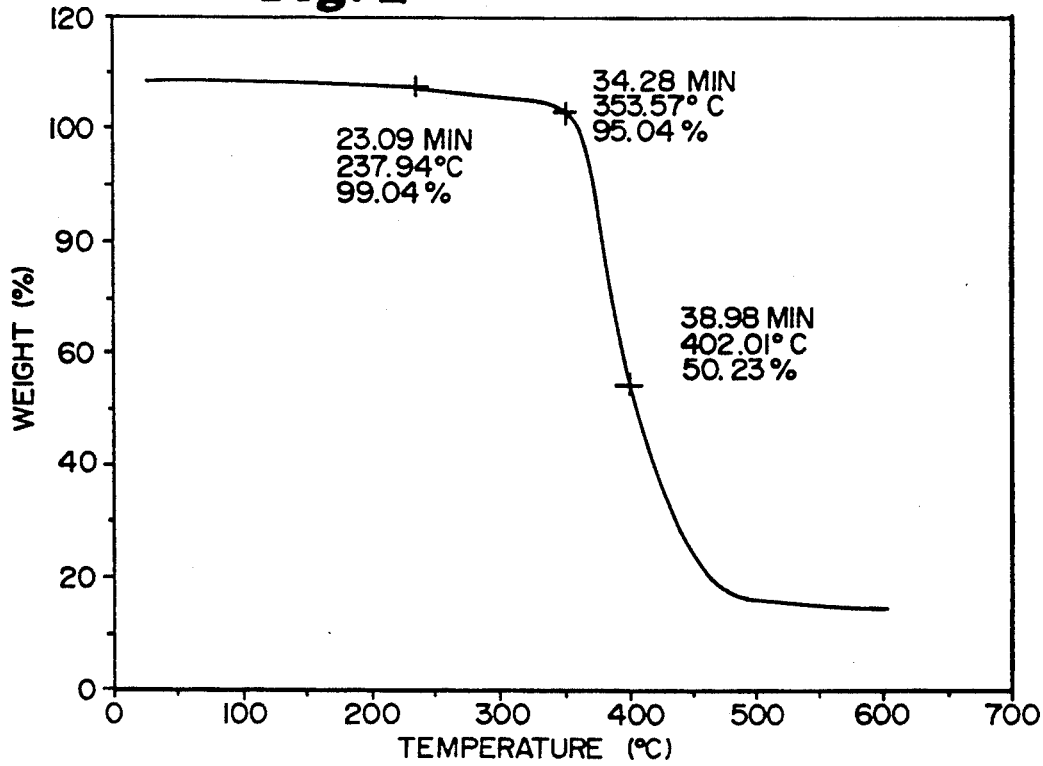
FIG. 2 is a TGA trace of a formulation of the invention described in Example 2.

The above listed formulation was prepared and UV cured in the same manner as Formulation (II) on an ambient temperature mold:

FIG. 1 represents the TGA trace of (I), and shows that 1% weight loss occurs at approximately 188° C. In contrast, the same degree of weight loss occurs at a temperature approximately 50° C. higher, at 238° C. for (II), as shown in FIG. 2. At a weight loss of 5% and greater, (I) and (II) exhibit very similar behavior. Since TNI is a more rigid material, it has a much narrower range of elasticity (0.25% maximum strain at room temperature). whereas (I) has a wider range, to approximately 0.5% strain.

Figure 3:
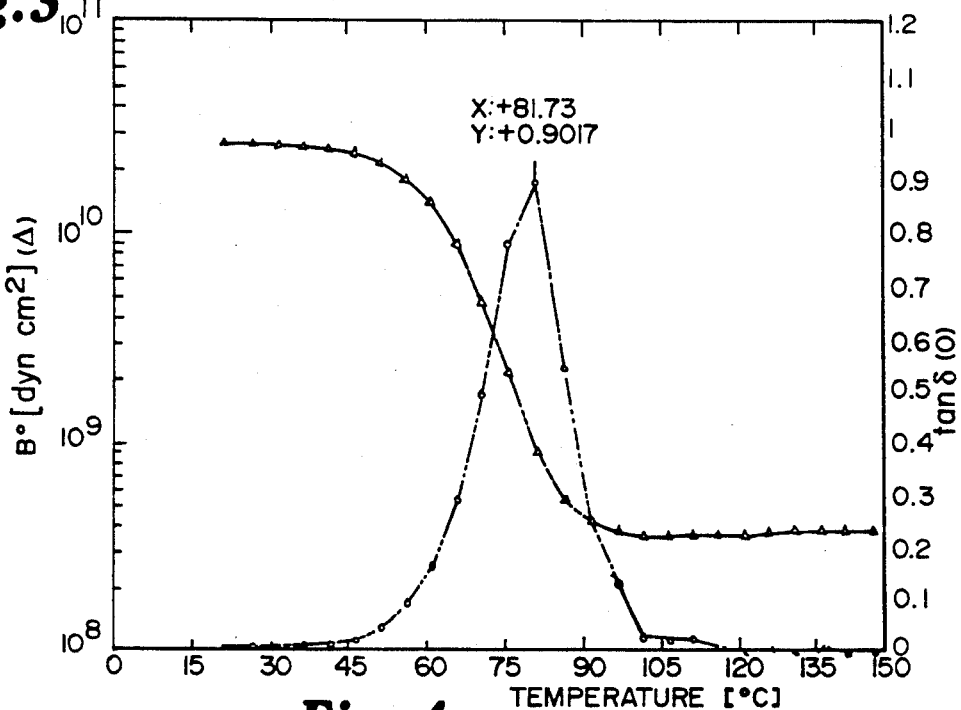
FIG. 3 is a DMA Temperature Sweep graph of the control formulation of Example 2.
Figure 4:
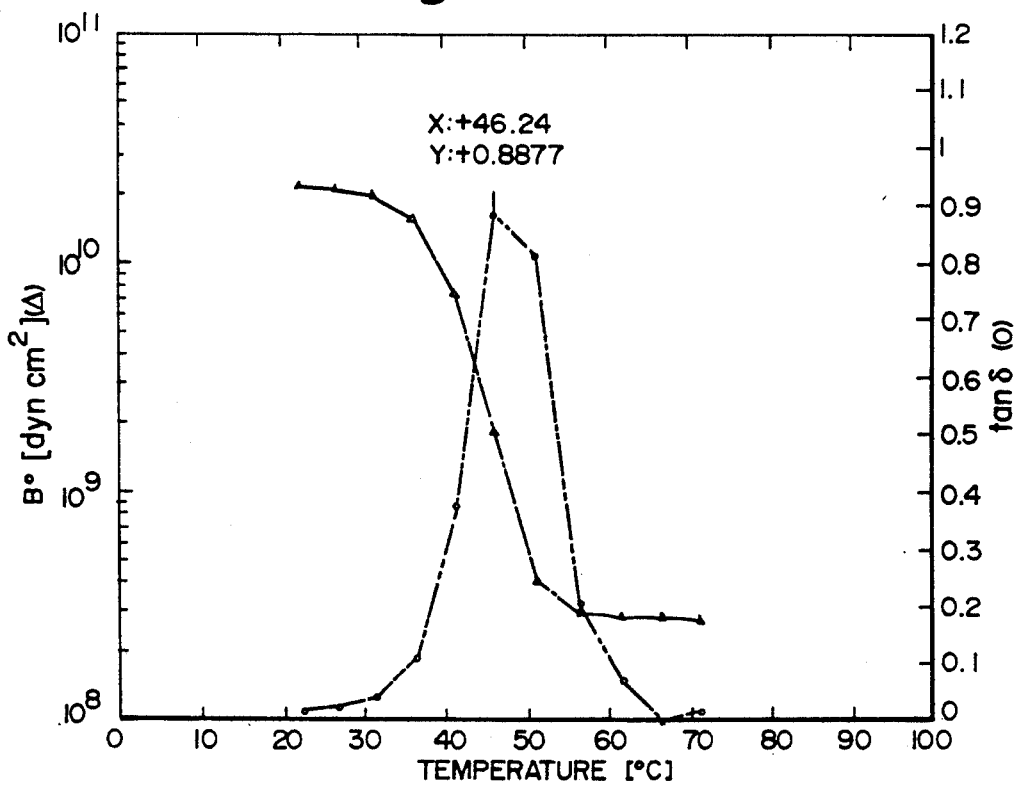
FIG. 4 is a DMA Temperature Sweep graph of the inventive formulation of Example 2.

As shown in FIGS. 3 and 4, the DMA temperature sweeps have shown that (II), FIG. 4, has a significantly higher Tg, at approximately 82° C., about 36° higher than (I), FIG. 3. This indicates greatly increased shear storage modulus in the temperature range of 46°-82° C. for (II), a desirable thermal advantage.

What is claimed is:

1. A tris(norbornenyl) isocyanurate compound of the formula:

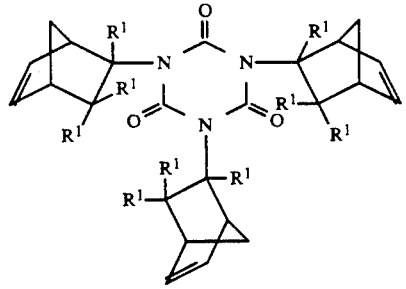

wherein $R^1$ is either hydrogen or an alkyl group.

2. A tris(norbornenyl) isocyanurate compound as in claim 1 wherein $R^1$ is hydrogen.

3. A tris(norbornenyl) isocyanurate compound as in claim 1 wherein $R^1$ is a methyl group.

4. A tris(norbornenyl) isocyanurate compound as in claim 1 prepared from the base-catalyzed trimerization of norbornenyl isocyanate.

5. A curable thiol-ene composition comprising a compound having a plurality of thiol groups and a compound as in claim 1.

6. A curable thiol-ene composition as in claim 5 containing a difunctional norbornenyl compound, a polyfunctional thiol and a crosslinker, the crosslinker comprising a compound as in claim 1.

7. A compound as in claim 1 having a melting point of 152°-155° C.

* * * * *

UNITED STATES PATENT AND TRADEMARK OFFICE
CERTIFICATE OF CORRECTION

PATENT NO. : 5,182,360
DATED : January 26, 1993
INVENTOR(S) : Anthony F. Jacobine et al It is certified that error appears in the above—identified patent and that said Letters Patent is hereby corrected as shown below:

Col. 6, line 35, after "compound" delete ", a polyfunctional thiol and crosslinker, the crosslinker comprising a compound as in claim 1"

Col. 6, line 34, after "5" insert -- further --

Signed and Sealed this

Twenty-sixth Day of October, 1993

Attest:

BRUCE LEHMAN

Attesting Officer     Commissioner of Patents and Trademarks